(12) United States Patent
Elmouelhi et al.

(10) Patent No.: US 8,152,804 B2
(45) Date of Patent: *Apr. 10, 2012

(54) TRANSURETHRAL NEEDLE ABLATION SYSTEM

(75) Inventors: Ahmed Elmouelhi, Minneapolis, MN (US); Mark A. Christopherson, Shoreview, MN (US); John M. Swoyer, Andover, MN (US); Shahn S. Sage, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1286 days.

This patent is subject to a terminal disclaimer.

(21) Appl. No.: 11/833,107

(22) Filed: Aug. 2, 2007

(65) Prior Publication Data
US 2008/0021445 A1    Jan. 24, 2008

Related U.S. Application Data

(63) Continuation of application No. 10/964,551, filed on Oct. 13, 2004, now Pat. No. 7,261,710.

(51) Int. Cl.
*A61B 18/14* (2006.01)
(52) U.S. Cl. .......................... 606/41; 607/101
(58) Field of Classification Search .............. 606/41, 606/48–50; 607/96, 101, 102, 113
See application file for complete search history.

(56) References Cited

U.S. PATENT DOCUMENTS

| | | | |
|---|---|---|---|
| 2,784,603 A | 3/1957 | Collins | |
| 3,144,020 A | 8/1964 | Zingale | |
| D284,219 S | 6/1986 | Green et al. | |
| 5,370,675 A | 12/1994 | Edwards et al. | |
| 5,383,874 A | 1/1995 | Jackson et al. | |
| 5,400,267 A | 3/1995 | Denen et al. | |
| 5,531,676 A | 7/1996 | Edwards et al. | |
| 5,536,240 A | 7/1996 | Edwards et al. | |
| 5,651,780 A | 7/1997 | Jackson et al. | |
| 5,762,626 A | 6/1998 | Lundquist et al. | |
| 5,807,309 A | 9/1998 | Lundquist et al. | |
| 5,849,011 A * | 12/1998 | Jones et al. | 606/47 |
| 5,964,756 A * | 10/1999 | McGaffigan et al. | 606/41 |
| 6,077,244 A | 6/2000 | Botich et al. | |
| 6,090,105 A | 7/2000 | Zepeda et al. | |
| 6,165,169 A | 12/2000 | Panescu et al. | |
| 6,221,071 B1 | 4/2001 | Sherry et al. | |
| 6,231,591 B1 | 5/2001 | Desai | |
| 6,238,393 B1 | 5/2001 | Mulier et al. | |
| 6,241,702 B1 | 6/2001 | Lundquist et al. | |
| 6,302,903 B1 | 10/2001 | Mulier et al. | |
| 6,315,777 B1 | 11/2001 | Comben | |
| D457,958 S | 5/2002 | Dycus et al. | |
| 6,387,092 B1 | 5/2002 | Burnside et al. | |
| 6,391,027 B1 | 5/2002 | Farin et al. | |

(Continued)

FOREIGN PATENT DOCUMENTS
EP    1 201 196    5/2002
(Continued)

*Primary Examiner* — Michael Peffley
(74) *Attorney, Agent, or Firm* — Shumaker & Sieffert, P.A.

(57) ABSTRACT

A one-piece, single-use disposable device for transurethral needle ablation (TUNA) of prostate tissue to alleviate BPH is disclosed. The device may include a flexible catheter tip including a rigid core and a flexible tip. The device may also include a single use lockout to help ensure that the device is used to perform only one ablation procedure on a single patient. The device may further include a simplified needle deployment mechanism and/or an automatic needle retraction mechanism.

20 Claims, 17 Drawing Sheets

U.S. PATENT DOCUMENTS

| | | |
|---|---|---|
| 6,402,742 B1 | 6/2002 | Blewett et al. |
| 6,409,722 B1 | 6/2002 | Hoey et al. |
| 6,419,690 B1 | 7/2002 | Mikus et al. |
| 6,440,127 B2 | 8/2002 | McGovern et al. |
| 6,461,296 B1 | 10/2002 | Desai |
| 6,471,698 B1 * | 10/2002 | Edwards et al. ............ 606/41 |
| 6,537,248 B2 | 3/2003 | Mulier et al. |
| 6,537,272 B2 | 3/2003 | Christopherson et al. |
| 6,551,300 B1 | 4/2003 | McGaffigan |
| 6,611,793 B1 | 8/2003 | Burnside et al. |
| 6,623,515 B2 | 9/2003 | Mulier et al. |
| 6,632,221 B1 | 10/2003 | Edwards et al. |
| 6,632,222 B1 | 10/2003 | Edwards et al. |
| 6,638,275 B1 | 10/2003 | McGaffigan et al. |
| 6,641,580 B1 | 11/2003 | Edwards et al. |
| 6,652,516 B1 | 11/2003 | Gough |
| 6,685,648 B2 | 2/2004 | Flaherty et al. |
| 6,706,039 B2 | 3/2004 | Mulier et al. |
| D496,997 S | 10/2004 | Dycus et al. |
| D535,027 S | 1/2007 | James et al. |
| D541,418 S | 4/2007 | Schechter et al. |
| 7,261,710 B2 | 8/2007 | Elmouelhi et al. |
| 7,335,197 B2 | 2/2008 | Sage et al. |
| 2001/0031941 A1 | 10/2001 | Edwards et al. |
| 2001/0039415 A1 | 11/2001 | Francischelli et al. |
| 2002/0002393 A1 | 1/2002 | Mitchell |
| 2002/0120260 A1 | 8/2002 | Morris et al. |
| 2002/0120261 A1 | 8/2002 | Morris et al. |
| 2002/0151884 A1 | 10/2002 | Hoey et al. |
| 2002/0177846 A1 | 11/2002 | Mulier et al. |
| 2002/0183740 A1 | 12/2002 | Edwards et al. |
| 2003/0073989 A1 | 4/2003 | Hoey et al. |
| 2004/0147917 A1 | 7/2004 | Mueller, Jr. et al. |
| 2005/0288664 A1 | 12/2005 | Ford et al. |
| 2006/0079881 A1 | 4/2006 | Christopherson et al. |
| 2007/0049929 A1 | 3/2007 | Catanese, III et al. |
| 2007/0179491 A1 | 8/2007 | Kratoska et al. |
| 2007/0179496 A1 | 8/2007 | Swoyer et al. |

FOREIGN PATENT DOCUMENTS

| | | |
|---|---|---|
| GB | 2 269 538 A | 2/1994 |
| WO | WO 93/25136 | 12/1993 |
| WO | WO 01/05318 A1 | 1/2001 |

* cited by examiner

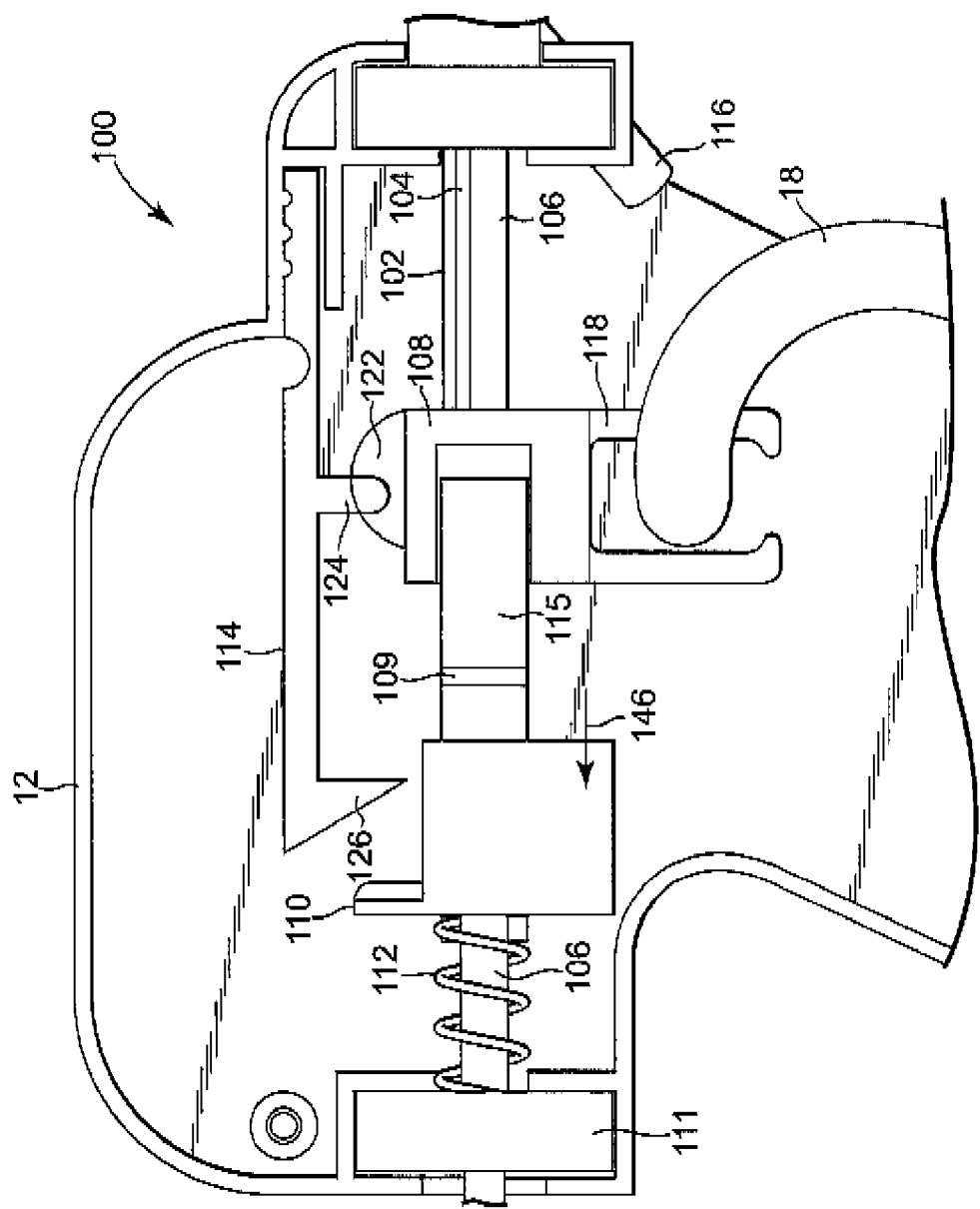

TRANSURETHRAL NEEDLE ABLATION SYSTEM

This application is a continuation of application Ser. No. 10/964,551, filed Oct. 13, 2004, now U.S. Patent No. 7,261,710, issued Aug. 28, 2007, the entire content of which is incorporated herein by reference.

FIELD OF THE INVENTION

The invention relates generally to prostate treatment and, more particularly, to techniques for transurethral treatment of benign prostatic hypertrophy (BPH).

BACKGROUND

Benign prostatic hypertrophy or hyperplasia (BPH) is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, urgency, decrease in urinary flow, nocturia, pain, discomfort, and dribbling.

One surgical procedure for treating BPH is transurethral needle ablation (TUNA). The TUNA technique involves transurethral delivery of an electrically conductive needle to the prostate site. The needle penetrates the prostate in a direction generally perpendicular to the urethral wall, and delivers electrical current to ablate prostate tissue. The electrical current heats tissue surrounding the needle tip to destroy prostate cells, and thereby create a lesion within the prostate gland. The destroyed cells may be absorbed by the body, infiltrated with scar tissue or become non-functional.

U.S. Pat. No. 5,807,309 to Lundquist et al. discloses an example of a transurethral ablation device that includes a disposable needle assembly. U.S. Pat. No. 5,964,756 to McGaffigan et al. describes another transurethral ablation needle device having a reusable handle and a replaceable cartridge assembly. Table 1 below lists documents that disclose devices for transurethral ablation of prostate tissue.

TABLE 1

| Pat. No. | Inventors | Title |
| --- | --- | --- |
| 5,807,309 | Lundquist et al. | Transurethral Needle Ablation Device and Method for the Treatment of the Prostate |
| 5,964,756 | McGaffigan et al. | Transurethral Needle Ablation Device with Replaceable Stylet Cartridge |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY

The present invention is directed to a one-piece, disposable device and method for transurethral needle ablation (TUNA) of prostate tissue to alleviate BPH. The device is designed to perform one ablation procedure on a single patient and then be discarded.

The device may include a flexible catheter tip including a rigid core and a flexible tip. The flexible tip provides increased comfort for the patient during insertion of the catheter into the urethra. The rigid core provides support to the flexible tip, and is open ended for delivery of fluid to cool the urethra. The device may also include a single use lock-out to help ensure that the device is used to perform only one ablation procedure on a single patient. The device may further include a simplified needle deployment mechanism and/or an automatic needle retraction mechanism.

Various embodiments of the present invention provide solutions to one or more problems existing in the prior art with respect to the ablation of prostate tissue. One problem, for example, is the requirement that a TUNA device, like most reusable medical devices, must be sterilized before it can be used to perform an ablation procedure on another patient. Sterilization introduces an unavoidable, fixed time delay between ablation procedures. To avoid this delay, the physician must either stock multiple TUNA devices so that procedures can be performed on several patients in sequence, or reduce the number of procedures performed in a given period of time to allow for sterilization of the TUNA device.

Another problem encountered with TUNA therapy is discomfort for the patient during insertion of the catheter within the urethra. At the beginning of an ablation procedure, the TUNA catheter is inserted at the tip of the penis and traverses the length of the urethra until the distal end of the catheter is properly positioned with respect to the target tissue. Even with the various types of anesthesia used during a typical TUNA procedure, including both local and topical anesthesias, insertion of the catheter into the urethra may be uncomfortable for many patients.

Another problem may arise with TUNA devices having a disposable catheter cartridge and a reusable handle. This type of device suffers from the same sterilization problem described above. Although the catheter cartridge is designed for single-use and is disposable, the reusable handle still requires sterilization between procedures. In addition, assembly of the cartridge and the handle is required before the procedure can be performed. Users may have difficulty assembling the device, or may fail to properly assemble the device. Either case results in an inefficient procedure for both the physician and the patient. Even when there are no difficulties with assembly, this type of device requires a certain amount of pre-procedure preparation time for assembling the catheter cartridge and the handle.

Another problem with conventional TUNA devices is the need to maintain the device itself. By their very nature, reusable devices intended for long term use require a certain amount of upkeep to keep them in proper working order. Some of this maintenance can be done at the hospital, clinic or other location close to the physician. Other times, the device must be returned to the manufacturer. For example, in addition to scheduled, periodic maintenance, the devices may sometimes need to be returned to the manufacturer for more intensive maintenance, such as when a device failure occurs. In any event, some conventional TUNA devices will at times be unavailable due to maintenance. Physicians may therefore have to stock a greater number of TUNA devices to ensure a desired patient throughput, or reduce the number of procedures performed in a given amount of time.

Another problem arises from the nature of the TUNA procedure itself. In a typical TUNA procedure, multiple ablations may be performed at different locations throughout the prostate. After ablation of tissue in one location is complete, the physician may retract the needles into the catheter, rotate and reposition the catheter within the urethra, and deploy the needles at a different tissue location. At times, however, the physician may fail to fully retract the needles before repositioning the catheter. For example, the physician may attempt to but inadvertently fail to fully retract the needles or may forget to retract the needles entirely before attempting to reposition the device within the urethra. When the catheter is repositioned within the urethra, the still fully or partially deployed needles may cause damage to the prostate and/or the urethra, as well as result in increased patient pain and longer recovery times.

Various embodiments of the present invention may posses one or more features to solve at least one of the foregoing problems. For example, the present invention overcomes at least some of the disadvantages of the foregoing procedures by providing a one-piece, disposable device for transurethral needle ablation (TUNA) of prostate tissue to alleviate BPH. The device may be designed to perform one ablation procedure on a single patient and then be discarded. The device may be constructed of mostly plastic parts. The device may include a single use lock-out to help ensure that the device is not inadvertently used on more than one patient. The device may also include a flexible catheter tip. In addition, the device may include a simplified needle deployment mechanism. As a further feature, the device may include an automatic retraction mechanism.

The invention also provides a transurethral ablation procedure embodied by a method for use of the ablation device described above. The method involves, for example, inserting a distal end of a transurethral needle ablation catheter into a urethra of a male patient, deploying at least one ablation needle, applying ablation energy via the ablation needle, withdrawing the catheter from the urethra, and disposing of the transurethral needle ablation device after the ablation procedure is complete.

In comparison to known implementations of transurethral needle ablation, various embodiments of the present invention may provide one or more advantages. Because the device is designed for one-time use, sterilization is not required. This may minimize preparation time between procedures as well as result in higher patient throughput. In addition, the one-piece design of the device means that no pre-procedure assembly is required, further reducing preparation time. Furthermore, time spent maintaining the device may be reduced or eliminated as the device is used only once and then discarded. In addition, because the device may include a simplified design constructed of mostly plastic parts, the resulting TUNA device may be more reliable, easier to manufacture, lighter in weight and easier for the physician to operate and maneuver. These features may result in a transurethral ablation device that enables the physician to perform faster, more accurate, and more efficient TUNA procedures.

As another advantage, the flexible catheter tip may provide increased patient comfort during insertion of the catheter into the urethra. As another advantage, the single use lockout helps to ensure that the device is used on only a single patient. In this way, the patient receives the benefit of a dedicated TUNA device, increasing procedural safety.

As yet another advantage, the simplified needle deployment mechanism may result in a TUNA device that is more reliable, easier to manufacture, lighter and easier for the physician to maneuver. As yet another advantage, the automatic needle retraction mechanism helps ensure full retraction of the needles. The automatic needle retraction feature thus may increase the safety of the procedure by reducing the likelihood of inadvertent failure to fully retract the needles before the catheter is repositioned within or withdrawn from the urethra, thus reducing the likelihood of damage to the prostate or the urethra, and the associated increases in patient pain and recovery time.

Thus, the invention can reduce the complexity of the ablation procedure, while increasing efficiency, convenience and safety. The invention can also result in a procedure in which the risk of damage to the urethra, patient pain and recovery times are minimized, thus further promoting patient safety and procedural efficacy.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features and advantages of the invention will be apparent from the description and drawings, and from the claims.

BRIEF DESCRIPTION OF DRAWINGS

FIGS. 6A-6J are diagrams illustrating the design and operation of the needle deployment mechanism of the device of FIG. 1.

DETAILED DESCRIPTION

Figure 1:
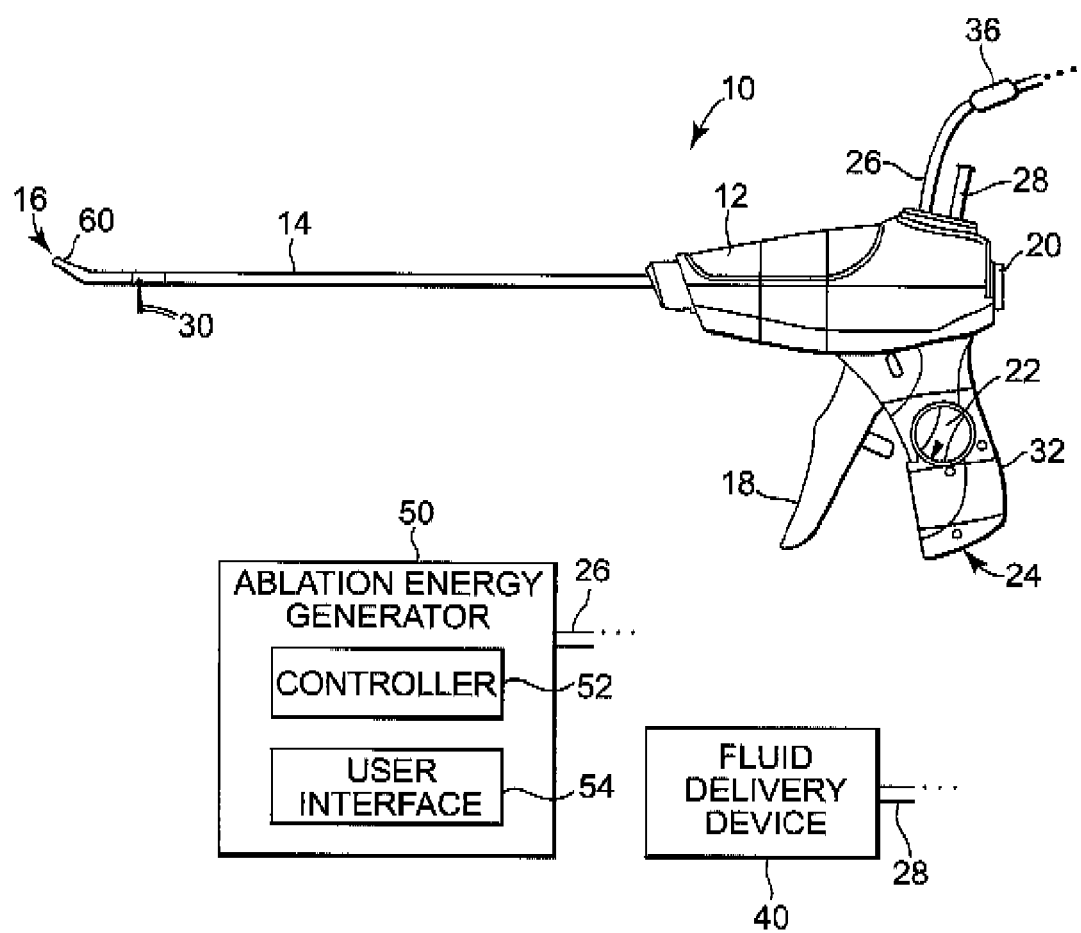
FIG. 1 is a schematic diagram illustrating a device for transurethral ablation of prostate tissue in accordance with the invention.

FIG. 1 is a schematic diagram illustrating a device 10 for transurethral needle ablation (TUNA) of prostate tissue. In one embodiment, device 10 is a one-piece, single use disposable device. The device may also include other features that will be apparent from this description.

As shown in FIG. 1, device 10 includes a housing 12 and a catheter 14 extending from the housing. A trigger-like lever 18 is actuated to advance electrically conductive ablation needles 30 from a distal end 16 of catheter 14. Device 10 may further include an endoscope 20 coupled to an endoscopic transducer (not shown) that extends along the length of catheter 14. Endoscopic viewfinder provides visualization of the urethra to assist the physician in positioning the distal end 16 and ablation needles 30 with respect to the target prostate tissue.

A fluid delivery tube 28 may be coupled to a fluid delivery lumen (not shown) that extends along the length of catheter 14 to deliver fluid to distal end 16. A proximal end of fluid delivery tube 28 is coupled to a fluid delivery device 40 that includes a reservoir containing a fluid and hardware to transmit the fluid to fluid delivery tube 28. For example, fluid delivery device 40 may include a pump, a syringe, or other mechanism to transmit the fluid. In some embodiments, the fluid may be an electrically conductive fluid such as saline.

An ablation current cable 26 is coupled to an electrical conductor that extends along the length of catheter 14 to needles 30. A proximal end of cable 26 is coupled to an ablation energy generator 50. An on/off switch 36 allows the physician to control power to the device 10. In the embodiment shown in FIG. 1, on/off switch 36 is located on ablation current cable 26. Ablation energy generator 50 may include a controller 52 that controls the ablation energy delivered to electrically conductive needles 30. Controller 52 may also control other aspects of the ablation procedure. Controller 52 may include one or more microprocessors, digital signal processors (DSPs), application-specific integrated circuits (ASICs), field-programmable gate arrays (FPGAs), or other equivalent logic circuitry. The image from endoscopic viewfinder 20 and other pertinent information concerning the ablation procedure may be acquired and processed via the ablation energy generator 50 and displayed on an associated graphical user interface 54 for view by a physician.

Ablation energy from ablation energy generator 50 is applied to the prostate tissue via ablation needles 30. Needles 30 may be constructed of a highly flexible, conductive metal such as nickel-titanium alloy, tempered steel, stainless steel, beryllium-copper alloy and the like. Nickel-titanium and similar highly flexible, shaped memory alloys are preferred. The needles 30 may be unipolar or bipolar. In the unipolar embodiment, ablation energy flows through each needle 30 while ground pads attached to the patient's skin act as return electrodes. In the bipolar embodiment, ablation energy flows between the needles 30 and through the surrounding prostate tissue to create a lesion. In another embodiment, a single needle 30 may be used. In that case, the ablation energy may flow between two electrodes carried by the single needle, or between the needle and a ground pad attached to the patient's skin, for example.

Device 10 may be configured to provide several alternative depths to which the needles may be deployed. Needle depth selector 22 allows the physician to control the amount that the needles extend from the distal end 16 of catheter 14 when deployed. As used herein, "needle depth" refers to the distance that a needle extends from the distal end 16 of catheter 14. Needle depth is measured from the needle exit port (see FIG. 4A, for example) at the distal end 16 of catheter 14 to the tip of a needle 30. In the embodiment shown in FIG. 1, the available needle depths are 12 mm, 14 mm, 16 mm, 18 mm, 20 mm and 24 mm, although many other needle depths could be provided and the invention is not limited in this respect.

The electrical ablation current produced by ablation energy generator 50 and delivered by needles 30 may be selected to provide pulsed or sinusoidal waveforms, cutting waves, or blended waveforms that are effective in producing the resistive/ohmic/thermal heating which kills cells within the target tissue. In addition, the electrical current may include ablation current followed by current sufficient to cauterize blood vessels. The characteristics of the electrical ablation current are selected to achieve significant cell destruction within the target tissue. The electrical ablation current may comprise radio frequency (RF) current producing power in the range of approximately 5 to 300 watts, and more preferably 5 to 50 watts, and can be applied for approximately 15 seconds to 3 minutes. If electrocautery is also provided via needles 19, then ablation energy generator 50 also may generate electrocautery waveforms.

Figure 2:
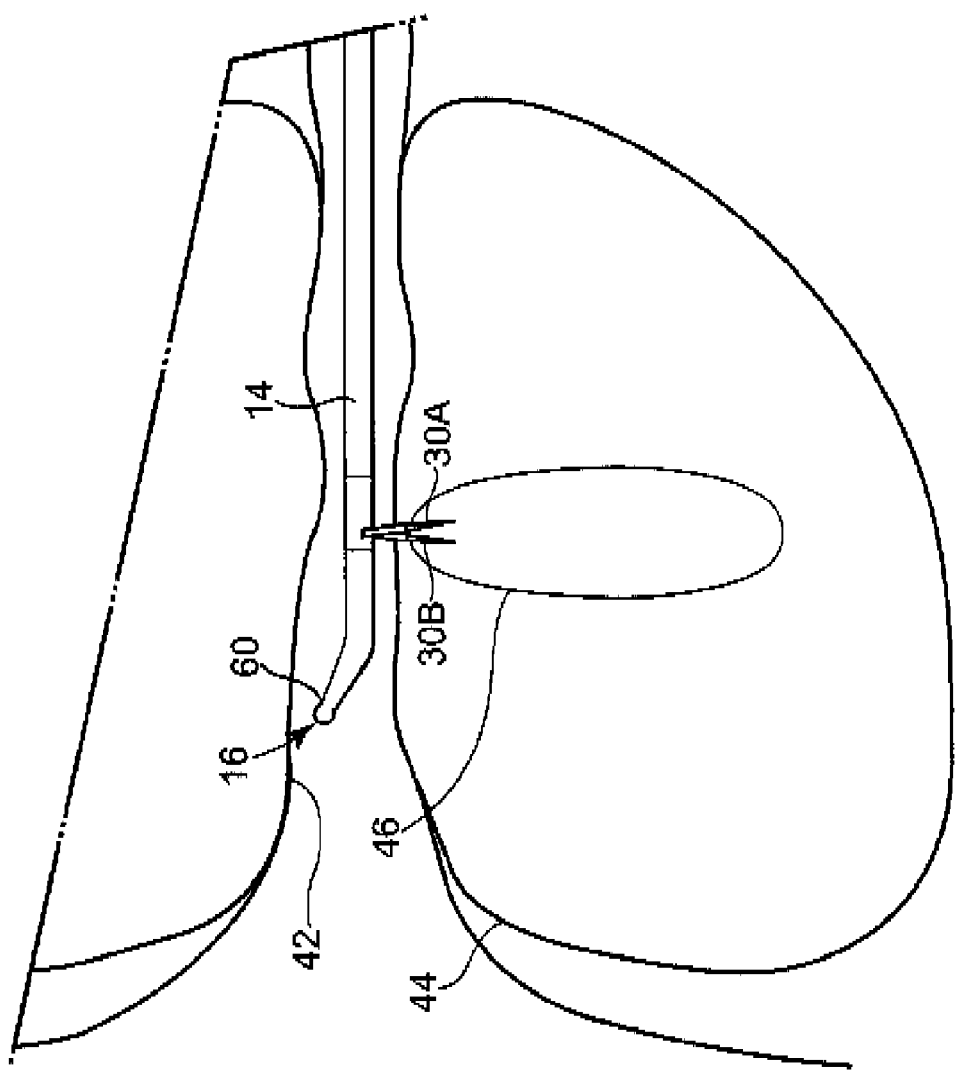
FIG. 2 illustrates the distal end of the device of FIG. 1 positioned to perform an ablation procedure within the urethra of a patient.

FIG. 2 shows a side view of the distal end 16 of the device of FIG. 1 inserted within a urethra 42 of a patient. Although an exemplary two-needle system is shown in FIG. 2, it shall be understood that single needle systems could also be used and that the invention is not limited in this respect. In addition, three, four or other multiple needle configurations could also be used without departing from the scope of the present invention.

In operation, a physician introduces catheter 14 into urethra 36 of a male patient, and advances the catheter so that distal end 16 is deployed adjacent to a prostate lobe, such as prostate lobe 44. Endoscopic viewfinder 20 may aid in positioning distal end 16 of catheter 14 relative to the prostate lobes.

The physician may actuate lever 18 (see FIG. 1) to drive needles 30 through the wall of urethra 42 and into prostate lobe 44. In some embodiments, catheter 14 may carry multiple pairs of ablation needles on opposite sides of the catheter to simultaneously access more than one prostate lobe.

Prior to activation of ablation energy generator 50 to deliver ablation current to needles 30, fluid delivery device 40 (see FIG. 1) may be activated to deliver fluid to the target tissue site within the urethra proximate prostate lobe 44. The fluid functions to cool the urethra during the ablation procedure. The fluid may be sufficiently viscous to provide a controllable flow within catheter 14 and out of distal end 16 of catheter 14. Fluid delivery device 40 may be activated to deliver the fluid before, during and/or after the ablation procedure. The fluid may also be a conductive fluid in embodiments where fluid is delivered via the needles or other means into the prostate tissue to create a wet electrode.

Upon penetration of needles 30 into prostate lobe 44 and delivery of the fluid, the needles 30 deliver ablation energy from ablation energy generator 50 to ablate the target tissue within the prostate lobe. After completion of an ablation, the physician may fully retract the needles back into the catheter, and rotate or otherwise reposition the catheter within the urethra to create additional lesions within the same prostate lobe 44, or to access and ablate another prostate lobe, if desired. After the completion of the ablation procedure, the needles are fully retracted into the catheter and the device is withdrawn from the urethra. In an embodiment where device 10 is a single use, disposable device, device 10 may then be discarded.

Figure 3A:
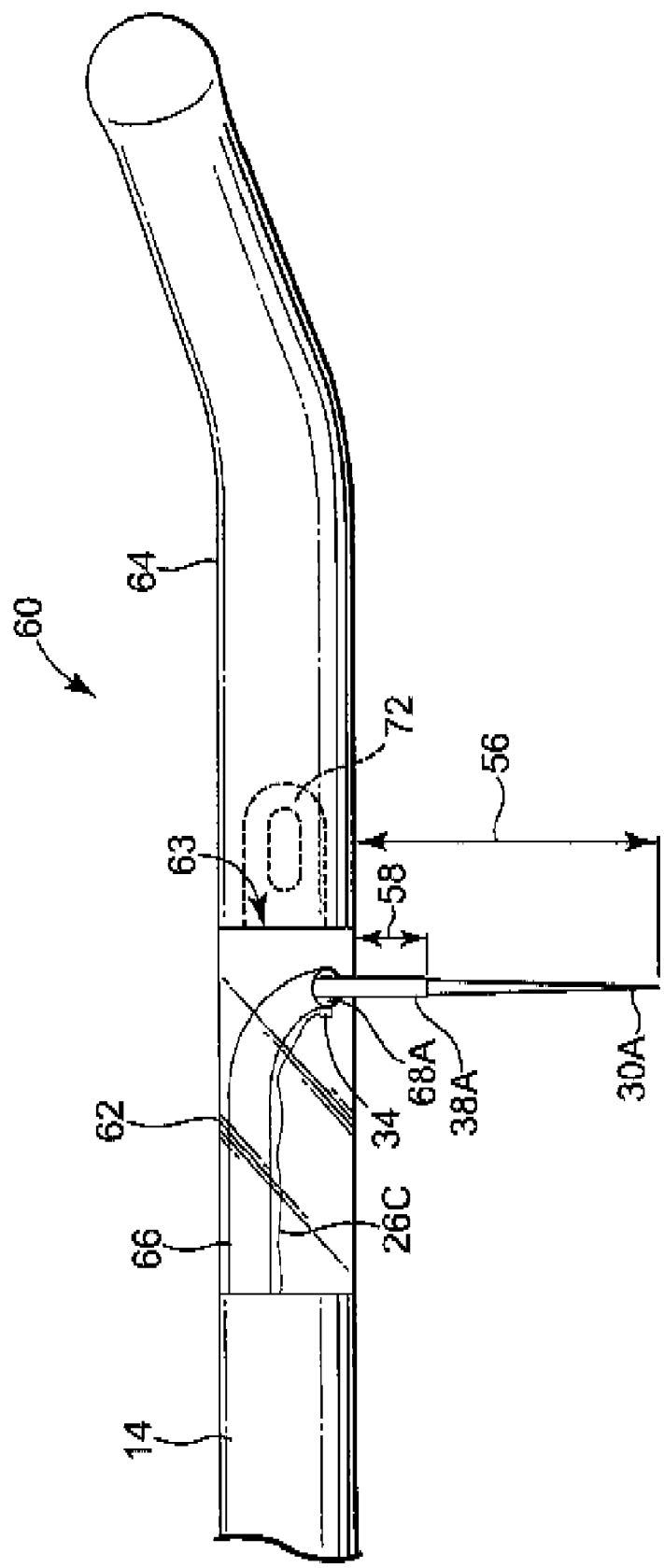
FIGS. 3A and 3B are side and bottom views, respectively, of the catheter tip at the distal end of the catheter of the device of FIG. 1.
Figure 3B:
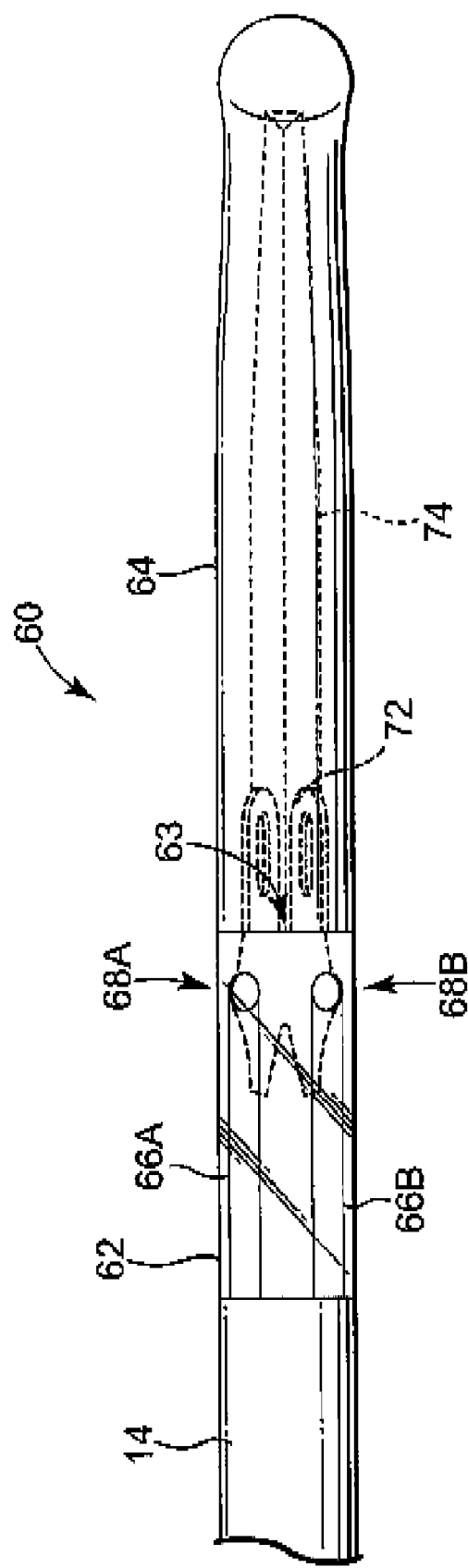

FIG. 3A shows a side view and FIG. 3B shows a bottom view of catheter tip 60 positioned at the distal end 16 of catheter 14 for the device of FIG. 1. Catheter tip 60 includes a rigid core 62 and a flexible tip 64. Flexible tip 64 is preferably fabricated of a suitable flexible material and provides increased patient comfort during insertion of catheter 14 into the urethra of the patient. Rigid core 62 provides support for the flexible tip 64 and also provides support for guide tubes 66. Catheter tip 60 also includes support structures 72 that serve to further support flexible tip 64 during insertion of the catheter into the urethra.

In one embodiment, rigid core 62 is fabricated from a material chosen to provide sufficient rigidity to adequately support guide tubes 66 and to provide support for flexible tip 64 during insertion into the urethra. Examples of suitable materials with which to construct rigid core 62 may include materials that are sufficiently rigid to provide support to the flexible tip during insertion into the urethra and to adequately support guide tubes 66. Other properties that may be considered are the ability to withstand a vacuum (for sterilization of the device at the time of manufacture), the ability to withstand the high temperatures experienced during an ablation procedure, biocompatibility and resistance to deformation. To provide sufficient rigidity, a material having a Shore A hardness of at least 70 may be used. In one embodiment, rigid core 62 is constructed using a thermoplastic elastomer, such as Versaflex™ OM 1060, available from GLS Corporation of McHenry, Ill.

In the embodiment shown in FIG. 3A, flexible tip 64 is substantially elbow-shaped. The flexibility and elbow shape of flexible tip may provide for more comfortable insertion of the catheter into the urethra. The material with which to construct flexible tip 64 may thus be chosen to be sufficiently flexible to allow for this more comfortable insertion. Other properties that may be considered when choosing a material with which to construct flexible tip 64 are the ability to withstand vacuum conditions, the ability to withstand high temperatures experienced during an ablation procedure, biocompatibility and resistance to deformation. To provide sufficient flexibility, a material having a Shore A hardness in the range of, for example, between 20 and 90, and preferably between 30 and 70, may be used. Examples of such materials include silicone, thermoplastic elastomers, and other types of medical grade rubbers. In one embodiment, flexible tip 60 may be constructed using a Versaflex™ thermoplastic elastomer, available from GLS Corporation of McHenry, Ill.

Rigid core 62 provides an open end 63 through which fluid may be delivered to cool the urethra during the course of the ablation procedure. The fluid may be delivered via fluid delivery tube 28 (see FIG. 1) that connects to a second fluid delivery tube (not shown in FIGS. 3A-3B) extending through the length of catheter 14. The fluid travels out the open end 63 of rigid core 62. A notch 74 on the side of needle exit from the catheter 14 assists in spreading the fluid to cool the urethra during the ablation procedure. Notch 74 may extend along at least a portion of the length of flexible tip 64 and may be substantially V-shaped to assist with spreading of the cooling fluid.

Catheter 14 includes guide tubes 66A and 66B extending from the proximal to near the distal end of rigid core 62. Needle exit ports 68A and 68B are formed in the wall of rigid core 62 by the guide tubes 66A and 66B, respectively. Needles 30A and 30B (needle 30B not shown) may be disposed adjacent one another in a substantially side-by-side relationship. Each needle 30A and 30B has a different insertion point into the prostate tissue, resulting in two different needle "sticks" through the prostate tissue. Each needle 30A and 30B is surrounded by an insulative sheath 38A and 38B, respectively. Insulative sheaths 38A and 38B may extend at least partially into the prostate upon deployment of the needle to protect the urethra from undesired ablation of the urethral wall.

Push rods (not shown) are connected at their proximal end to a needle deployment mechanism 100 (see FIGS. 6A-6J) for deploying the needles 30 and their corresponding sheaths 38. For example, the push rods may be operationally connected to lever 18 via needle deployment mechanism 100 for deploying the needles 30 out of the catheter tip and into the prostate tissue. The push rods serve to transfer the mechanical motion of lever 18 and thus "push" their respective needle 30 and sheath 38 out of the respective exit port 68 of the guide tube 66 and into the prostate tissue. In one embodiment, the needles 30 may be inserted into the same prostate lobe such that a larger lesion may be created within the prostate lobe during the ablation procedure. In another embodiment, the needles 30 may be arranged for simultaneous insertion into different prostate lobes.

Once deployed from the distal end 16 of the catheter 14, the needles 30A and 30B may be physically spaced apart such that they create a sufficiently large ablation zone. At the same time, the needles may be spaced sufficiently close so that they both penetrate the same prostate lobe. In addition, device 10 may be configured to provide several alternative needle depths. The needle depth is indicated in FIG. 3A by reference numeral 56. As used herein, "needle depth" refers to the distance that a needle is extended from the distal end 16 of catheter 14. Needle depth 56 is measured from the needle exit port at the distal end 16 of catheter 14 to the tip of the needle 30. In one embodiment, each needle 30A and 30B may have a total length in the range of approximately 12-22 millimeters, which may be adjustable by the physician as described above with respect to FIG. 1, or which may be fixed in some embodiments. However, any other appropriate needle depths could also be used, and the invention is not limited in this respect.

Insulative sheaths 38A and 38B may extend at least partially into the prostate upon deployment of the needle to protect the urethra from undesired ablation of the urethral wall. During needle insertion, needle deployment mechanism advances needles 30 and their respective sheaths 38 through the wall of the prostate and into the prostate tissue. In one embodiment, sheaths 38 are initially advanced to a depth of approximately 8-10 millimeters to ensure that the sheath remains partially extended into the prostate once the needles are fully deployed. This avoids the tenting effect that may be encountered when the needles are first inserted into the prostate tissue. After the sheath is advanced to the 8-10 millimeter depth, needle deployment mechanism 100 retracts the sheath back to a depth where it remains to protect the urethra during the ablation procedure. The "sheath depth" 58 is indicated in FIG. 3A. In one embodiment, for example, sheaths 38 extend approximately 6 millimeters from the needle exit ports 68 during application of ablation energy. However, it shall be understood that a 6 millimeter sheath depth is but one example of a sheath depth, and that other sheath depths could also be used. In another embodiment, sheaths 38 may be advanced directly to the desired depth, for example, 6 millimeters, without the initial overextension and subsequent partial retraction.

Thermocouple 34 is positioned on the outside wall of the distal end of guide tube 66. Thermocouple 34 may be welded or otherwise attached to the outside wall of the distal end of guide tube 66 and positioned near exit port 68. In this position, thermocouple 34 may accurately measure the temperature of the urethra during the ablation procedure while being protected from movement of the needle and the sheath during deployment and retraction of the needles 30. Accurate temperature sensing may be provided due to the thermally conductive properties of the stainless steel or other material used to construct guide tubes 66. Heat generated in the urethra during an ablation procedure may be thermally conducted through the guide tube where it may be sensed by thermocouple 34. Ablation energy generator 50 receives this temperature information via connector 35 and ablation current cable 26. Controller 42 analyzes the temperature information and may control the application of ablation energy to ensure that the urethral temperature remains at a safe level. In one embodiment, a single thermocouple 34 attached to one of the guide tubes, for example, either one of guide tubes 66A or 66B, provides the temperature information. In another embodiment, two thermocouples, one associated with each guide tube 66A and 66B may be included to provide additional temperature sensing or to provide redundancy in case of hardware failure.

Figure 4:
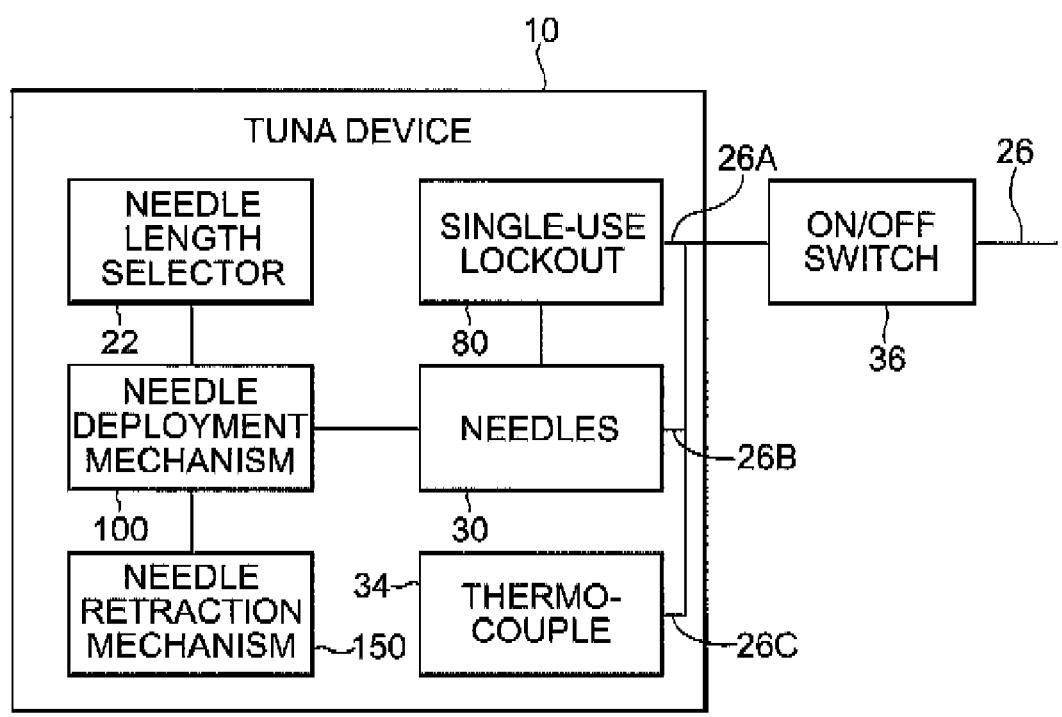
FIG. 4 is a block diagram of the device of FIG. 1.

FIG. 4 shows a block diagram of a TUNA device 10 such as that shown in FIG. 1. On/off switch 36 on ablation current cable 26 allows a physician to electrically connect ablation energy generator 50 to device 10 for communication of status information with controller 52 and for delivery of ablation current to the electrically conductive needles 30. Once inside device 10, cable 26 may include three separate connection lines; line 26A allows controller 52 to query single-use lock-out to obtain device usage information to help ensure that device 10 is not used on more than one patient, line 26B delivers ablation energy from ablation energy generator 50 to the electrically conductive needles 30, and line 26C allows controller 52 to receive temperature information from thermocouple 34.

Needle depth selector 22 allows a physician to select a desired needle depth from among several available needle depths. Needle deployment mechanism 100 advances needles 30 out of the distal end of the catheter and into the target tissue, controlling the advancement to the desired needle depth as determined by needle depth selector 22. Needle deployment mechanism 100 is described in more detail with respect to FIGS. 6A-6J. Needle retraction mechanism 150 automatically fully retracts needles 30 back into the catheter so that device 10 may be repositioned within the urethra to ablate a different target tissue site or so that the catheter may be safely withdrawn from the urethra upon completion of the ablation procedure. Needle retraction mechanism 150 is described in more detail with respect to FIG. 7.

Thermocouple 34 is positioned on an outer wall of a guide tube at the distal end of catheter near the exit ports for needles 30 (see FIG. 3A). Thermocouple 34 measures the temperature of the surrounding tissue to prevent overheating of the tissue during an ablation. The ablation energy generator receives temperature information from the thermocouple along ablation current cable line 26C. Controller 52 (see FIG. 1) may control application of the ablation energy based on the received temperature information, for example, to prevent overheating and burning of the target tissue or the urethra.

Single-use lockout 80 helps to ensure that the device 10 is not inadvertently used on more than one patient. Specifically, single-use lockout stores information concerning usage of the device 10. This device usage information may then be used to determine whether the device has been previously used on a different patient. For example, single-use lockout 80 may store usage information concerning, for example, a total amount of time elapsed since the first delivery of ablation energy (a total time of use), a total amount of time that device 10 has delivered ablation energy (a total ablation time), and/or a count of a total number of times that device 10 has delivered ablation energy (an ablation count).

Figure 5A:
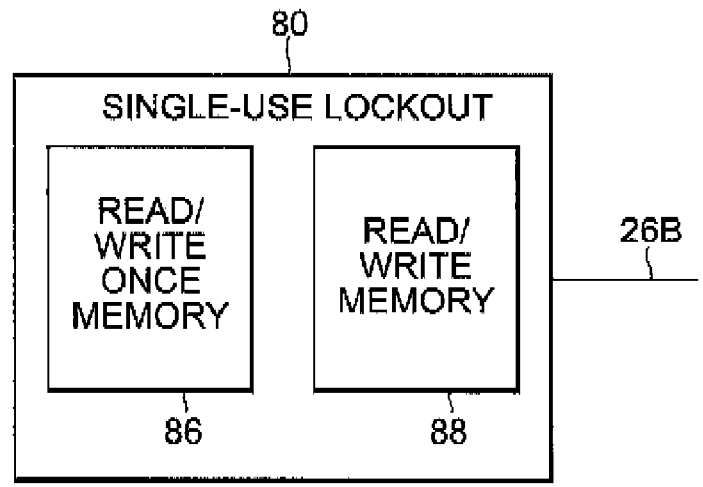
FIG. 5A is a block diagram of the single-use lock out feature for the device of FIG. 1.

FIG. 5A shows a block diagram of single-use lockout 80. Single-use lockout 80 is essentially a device specific memory chip for storing device usage information. This device usage information may be used to determine whether a device has been previously used on another patient. Single-use lockout 80 may include, for example, a read/write once memory 86 and a read/writable memory 88. Both read/write once memory 86 and read/writable memory 88 may be nonvolatile memory so that they do not require power to maintain the stored device usage information.

Figure 5B:
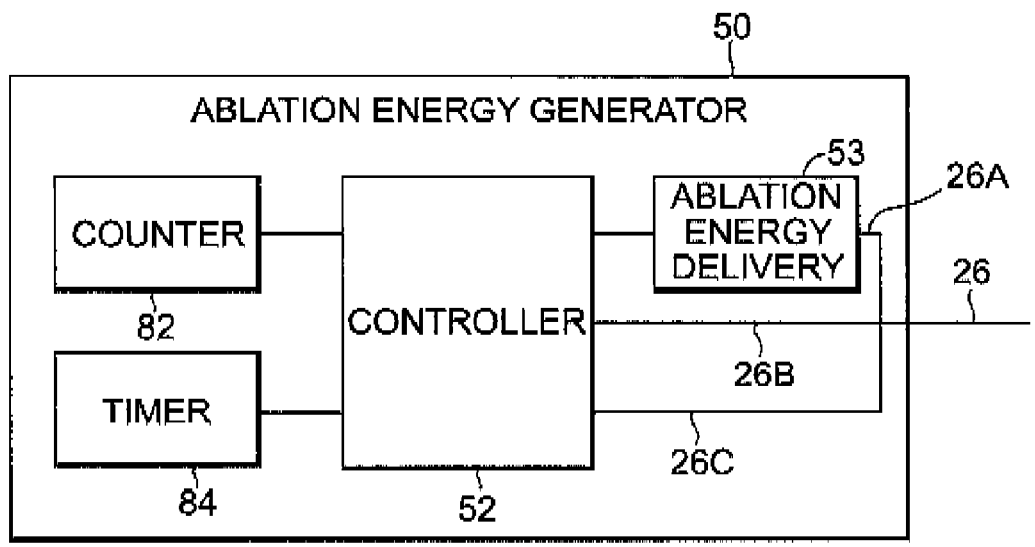
FIG. 5B is a block diagram of the ablation energy generator.

FIG. 5B shows a block diagram of ablation energy generator 50. Ablation energy generator includes controller 52, ablation energy delivery unit 53, counter 82 and timer 84. Counter 82 and timer 84 may be used to monitor device usage information, which is then written to single-use lockout 80 located within device 10. The monitored device usage information may include, for example, an absolute calendar time of first use (e.g., the actual calendar time, including day, month, and year as well as the hour, minute and second at which ablation energy is first applied to the patient) a total elapsed calendar time of use (e.g., the total amount of time elapsed since the absolute calendar time of first use), a total amount of time that ablation energy is delivered, a count of a total number of times that ablation energy is delivered, and/or some other appropriate parameter which may indicate whether the device has been previously used on a different patient.

Timer 84 may include a real-time clock that may be used to monitor the time of first use, and the total elapsed time of use. Timer 84 may also monitor the total amount of time that ablation energy is delivered to needles 30. Counter 82 may count the number of times that ablation energy is delivered to the needles 30. Controller 52 may write the monitored device usage information to single-use lockout 80 via line 26B for storage in one of read/write once memory 86 or read/writable memory 88.

For example, the absolute calendar time of first use may be stored in read/write once memory 86. Storing the absolute calendar time of first use in a memory that may not later be overwritten may prevent unauthorized tampering with device 10 and thus further help to ensure that device 10 is not used on more than one patient. The total elapsed calendar time of use, the total amount of time that ablation energy is delivered and the counted number of times that ablation energy is applied may be stored in read/writable memory 88. Storing this information in read/writable memory 88 allows controller 52 to periodically update the information throughout the course of the ablation procedure.

When device 10 is powered on via switch 36, controller 52 may query single-use lockout 80 along line 26B to obtain the stored device usage information. Controller 52 may then control delivery of ablation energy by ablation energy delivery unit 53 to the needles 30 based on the stored device usage information. For example, controller 52 may enable delivery of ablation energy if the stored device usage information indicates that device 10 has not been used on a previous patient. On the other hand, controller 52 may disable delivery of ablation energy if the stored device usage information indicates that device 10 has been used on a previous patient.

To determine whether the device 10 has been previously used and to appropriately control delivery of ablation energy, controller 52 compares the stored device usage information with various parameters to determine whether a device 10 has been previously used to perform ablations on another patient. These parameters may include, for example, a maximum allowable elapsed time of use, a maximum allowable amount of time that ablation energy may be delivered by the device (a maximum allowable ablation time), a maximum number of times the device may deliver ablation energy to the target prostate tissue, and/or some other appropriate parameter which may indicate whether the device has been previously used on a different patient.

Controller 52 may compare the stored device usage information with these parameters to determine whether the device has been previously used. By querying single use lock-out 80 and receiving the stored device usage information, controller 10 can determine, for example, whether the maximum allowable elapsed time of use of device 10 has been exceeded, whether the maximum allowable ablation time has been exceeded and/or whether a maximum number of ablations have been previously performed using device 10. If one or more of these parameters indicates that the device has been used on a previous patient, controller 52 may control ablation energy delivery unit 53 such that no ablation current is applied to needles 30. This may help prevent inadvertent or intentional use of the device on more than one patient. In addition, controller 52 may cause a corresponding error message to be displayed on user interface 54 (see FIG. 1) to alert the physician that device 10 has been used before and should be discarded. Ablation energy generator 50 may also continuously query single-use lockout after power-on to minimize the risk that device 10 will be used to perform ablations on multiple patients without switching device 10 off between procedures.

The maximum allowable elapsed time of use, the maximum allowable ablation time and the maximum number of allowed ablations may be chosen to provide a reasonable amount of time and a reasonable number of ablations to complete an entire ablation procedure on a single patient but not so much time or so many ablations that the device 10 may be inadvertently used on more than one patient. The maximum allowable elapsed time of use and the maximum allowable ablation time may be based on, for example, the corresponding amounts of time in which the majority of ablation procedures should reasonably be completed. The maximum allowable elapsed time of use may be in the range of 2 to 5 hours, for example. Similarly, the maximum allowable time that ablation energy may be applied may in the range of 0.5 to 1.5 hours, for example. A specific embodiment may set the maximum allowable elapsed time of use at 4 hours and the maximum allowable ablation time at 75 minutes, for example. The maximum number of allowed ablations may be based on the number of ablations reasonably required in the majority of ablation procedures. The maximum number of allowed ablations may be in the range of 20-30 ablations, for example. A specific embodiment may set the maximum number of allowed ablations at 25 ablations, for example.

Single-use lockout 80 may also be used to store error information in the event that a malfunction occurs during an ablation procedure. If a malfunction occurs, controller 42 may write information concerning the error to either memory 86 or 88. The error information may include, for example, error codes indicative of the type of error that occurred and/or timing information concerning when the error took place. This error information may be later retrieved and analyzed by maintenance personnel when processing devices returned to the manufacturer to help identify the malfunction and why it occurred.

Figure 6A:
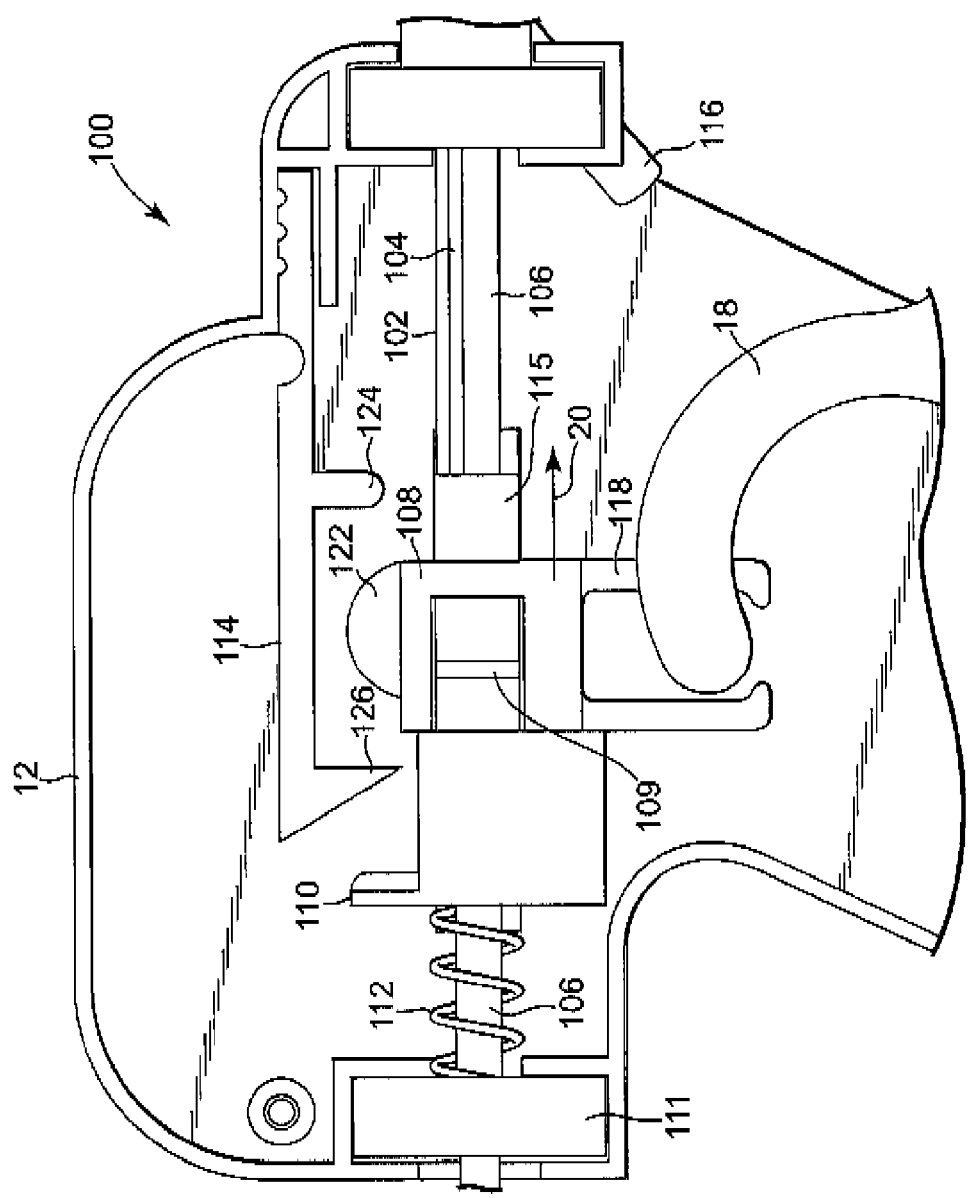

FIG. 6A is a side view of needle deployment mechanism 100 at rest inside housing 12 of a device 10 such as that shown in FIG. 1. Needle deployment mechanism 100 includes four main elements: needle block 108, sheath block 110, spring 112 and 6 mm catch 114. Needle block 108 actuates push rods 104 which deploy/retract needles 30. Similarly, sheath block 110 actuates push rods 102 which deploy/retract the needle sheaths. Sheath block 110 and needle block 108 are butted up next to each other, and are attached with snap fit 109. Spring 112 is attached to anchor block 111 and sheath block 110 and acts to pull sheath block 110 backward toward anchor block 111. 6 mm catch 114 includes a stop 126 and an extension 124.

An endoscope may be placed in scope tube 106 to allow a physician to view the placement of the distal end of the catheter 14 within the urethra. In addition, needle block 108 and sheath block 110 are slidably connected to scope tube 106. Actuation of lever 18 causes needle block 108 and sheath block 110 to move forward in the direction indicated by arrow 120 along scope tube 106.

In operation, the physician squeezes lever 18 to actuate needle engagement mechanism 118 attached to needle block 108. This causes needle block 108 to begin its forward movement in the direction indicated by arrow 120 to advance needles 30 into the prostate tissue.

Figure 6B:
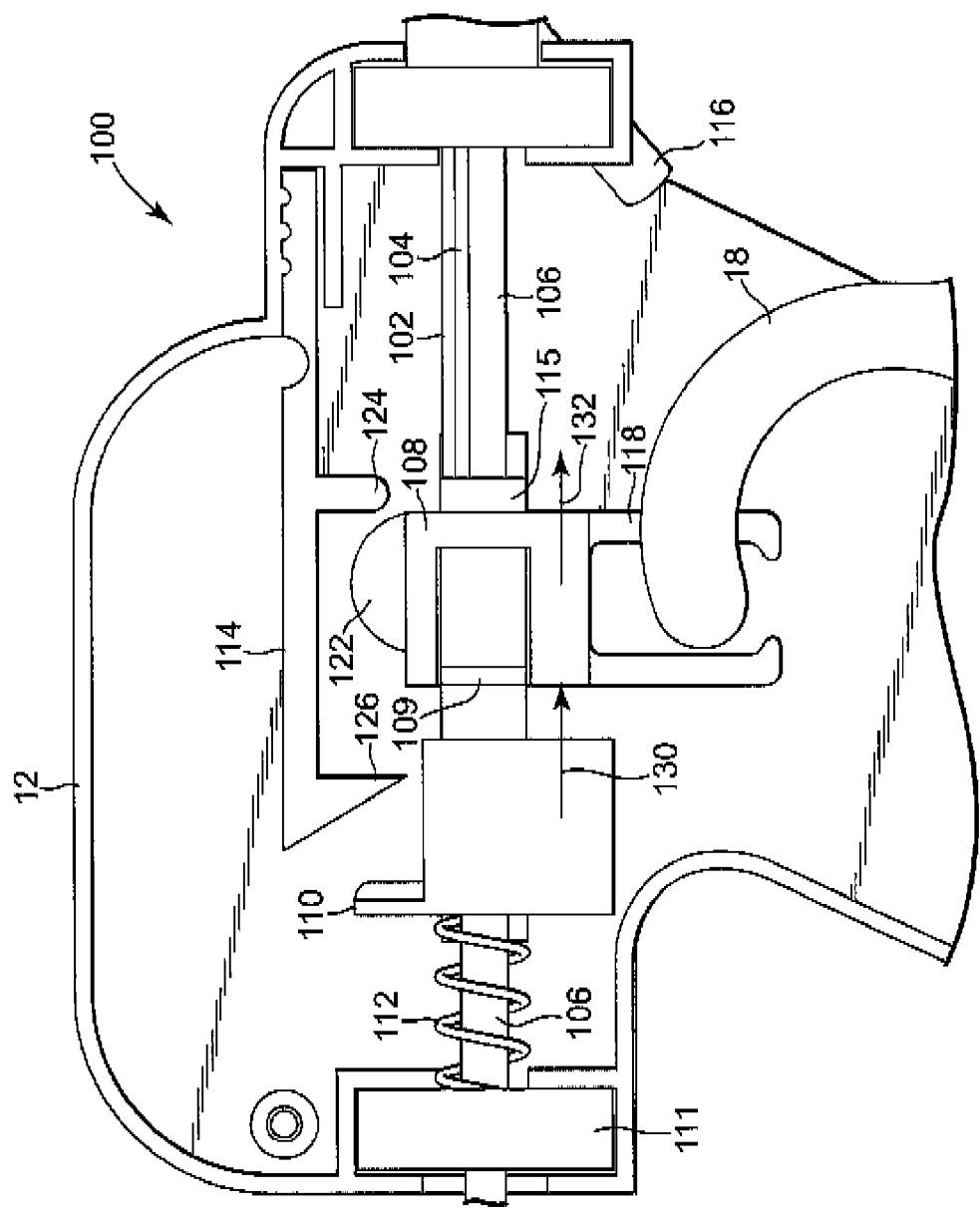

In FIG. 6B, because the needle block 108 and sheath block 110 are connected by snap fit 109, sheath block 110 moves forward along with needle block 108 in the directions indicated by arrows 130 and 132, respectively. As can be seen in FIG. 6B, sheath block 110 includes arms 115 that extend through needle block 108 and hold sheath block 110 and needle block 108 in place with respect to each other. At this point, needle block 108 and sheath block 110 move forward at the same rate.

Figure 6C:
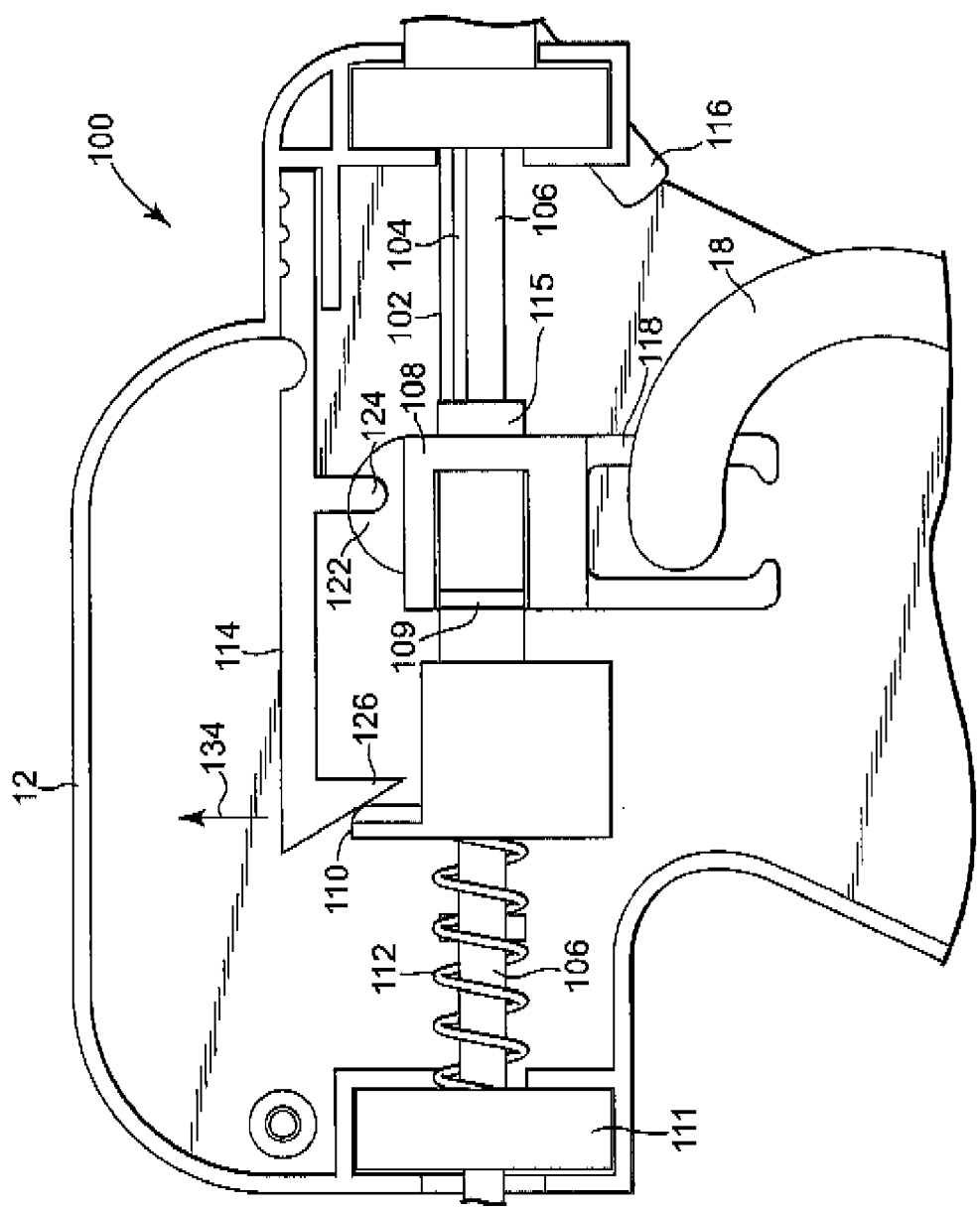

In FIG. 6C, slide cap 122 of needle block 108 hits extension 124 of 6 mm catch 114. This causes 6 mm catch 114 to move up in the direction indicated by arrow 134, allowing sheath block 110 to move forward.

Figure 6D:
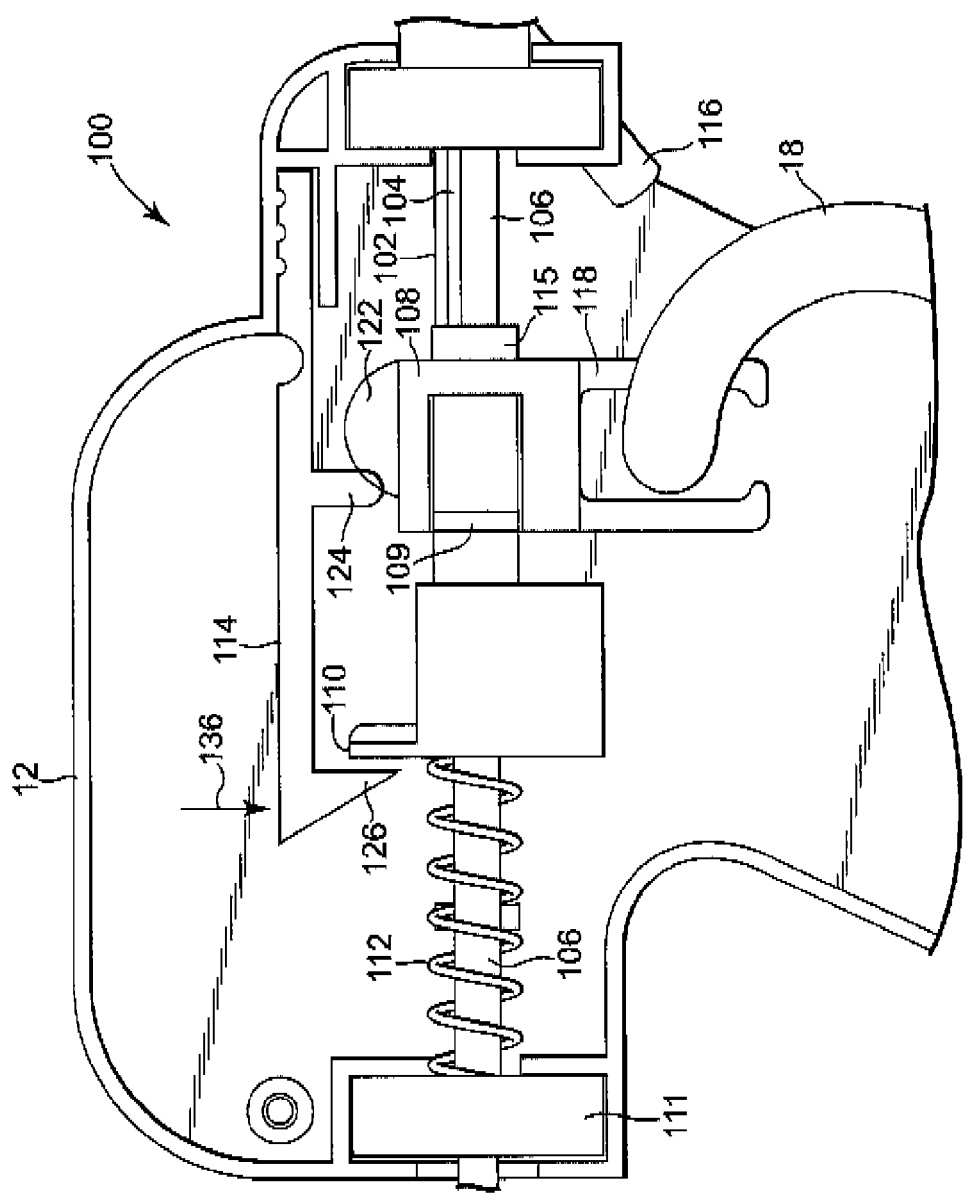

In FIG. 6D, needle block 108 and sheath block 110 are still moving forward together. As extension 124 moves past slide cap 122, 6 mm catch moves down in the direction indicated by arrow 136. Spring 112 continues to pull backward on sheath block 110, although sheath block 110 continues to move forward along with needle block 108 because of the connection provided by snap fit 109. At this point, the sheath and the needle are both extended substantially the same depth from the needle exit port at the distal end of catheter 14.

Figure 6E:
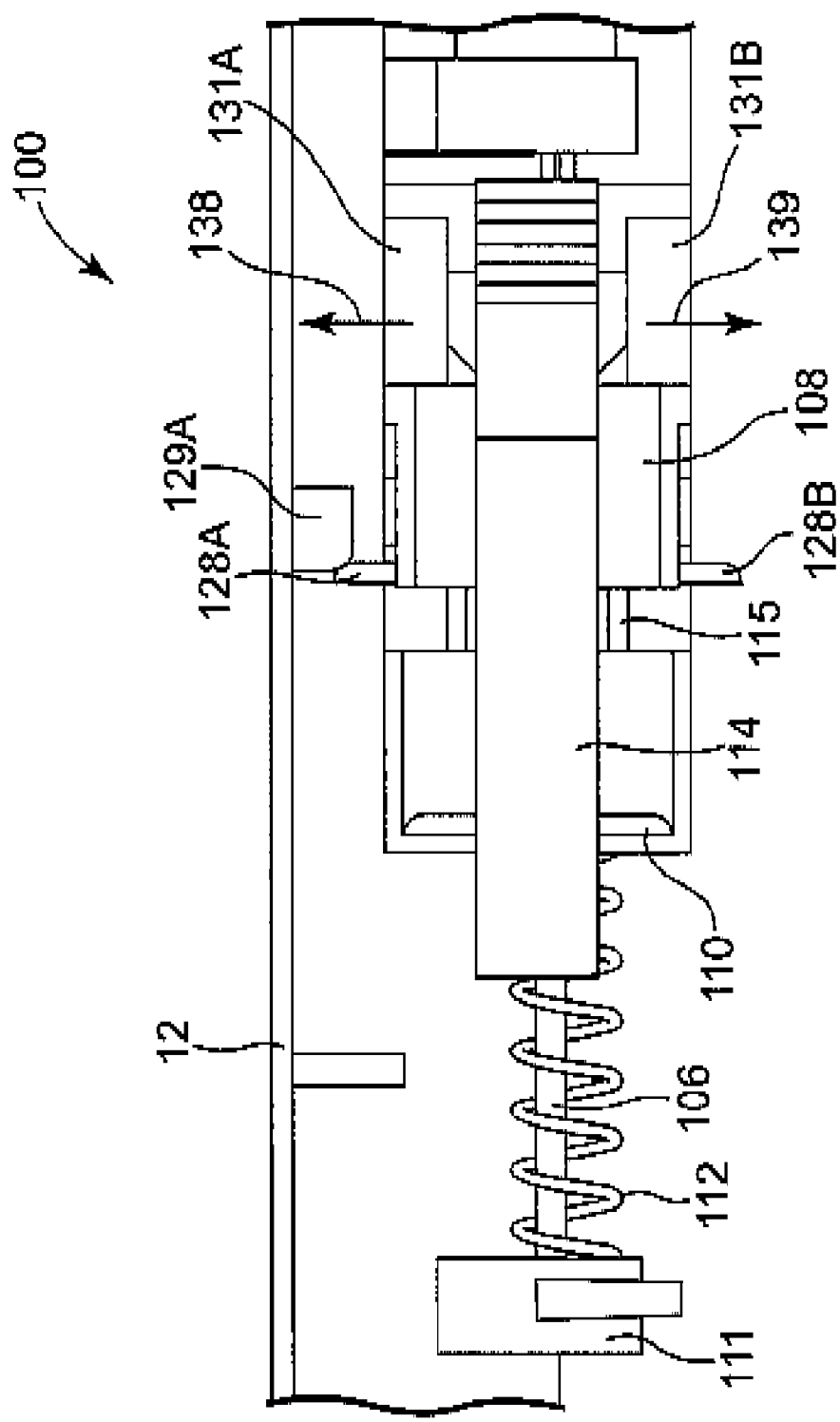

FIG. 6E is a top view of needle deployment mechanism 100. Sheath block 110 includes sideways tabs 128A and 128B. As sheath block 110 continues to move forward along with needle block 108, tabs 128A and 128B attached to sheath block 110 hit tab releases 129A and 129B (129B not shown) located in the sides of housing 12. Tab releases 129A and 129B push the tabs 128A and 128B back, causing movement of half arrows 131A and 131B in the direction indicated by arrows 138 and 139, respectively, releasing the snap fit 109. Once snap fit 109 is released, sheath block 110 is free of needle block 108 and the force applied by spring 112 pulls sheath block 110 backward. The spring pulls sheath block 110 back to stop 126 on 6 mm catch 114. As this occurs, the needle continues moving forward, while the sheath stops moving forward and is retracted back to the 6 mm position along with sheath block 110. 6 mm catch 114 may be adjusted to provide for a different sheath depth in embodiments where a sheath depth of other than 6 millimeters is used.

Figure 6F:
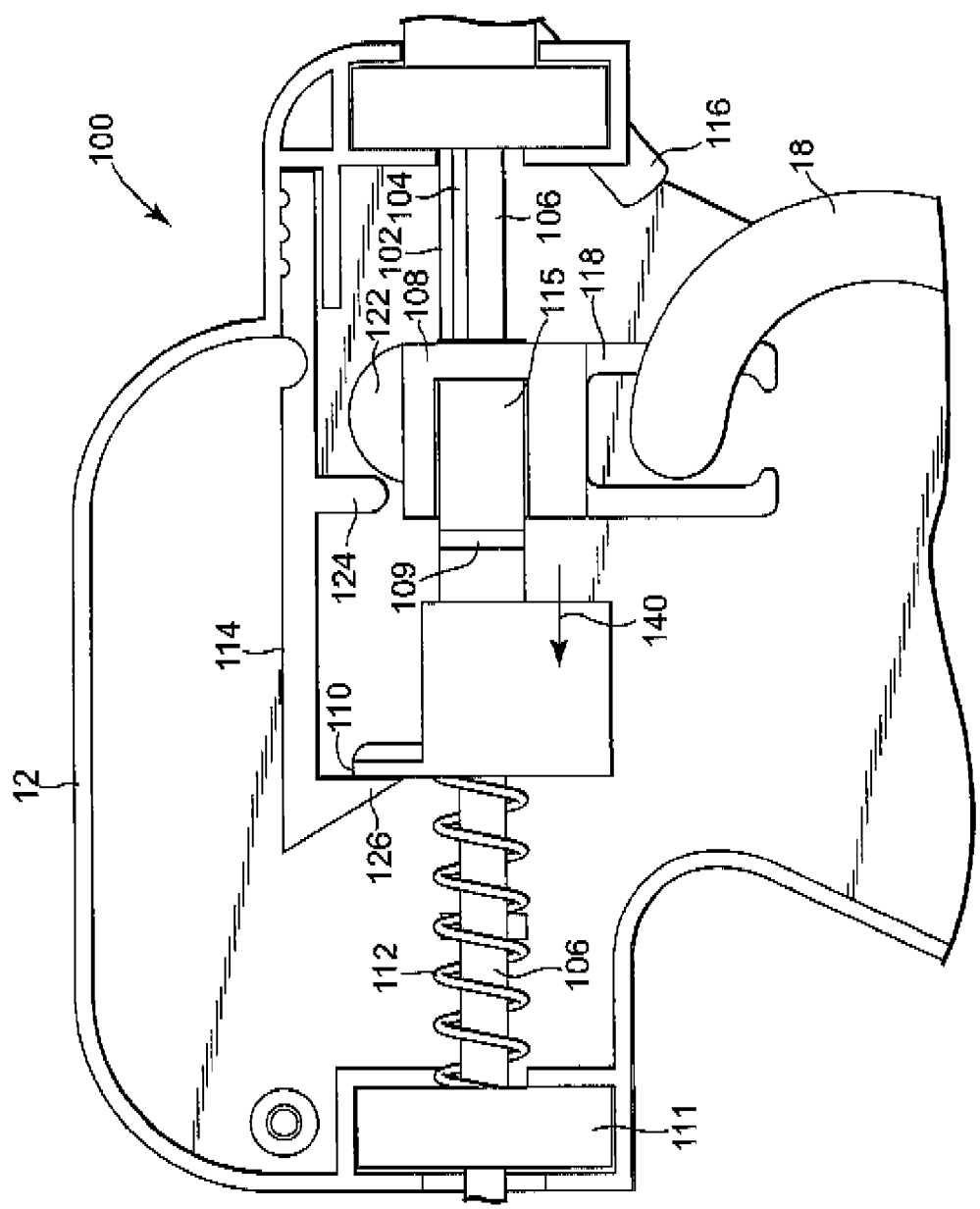

FIG. 6F is another side view of the needle deployment mechanism 100. In this view, sheath block 110 retracts back to 6 mm position determined by stop 126 on the 6 mm catch 114.

Figure 6G:
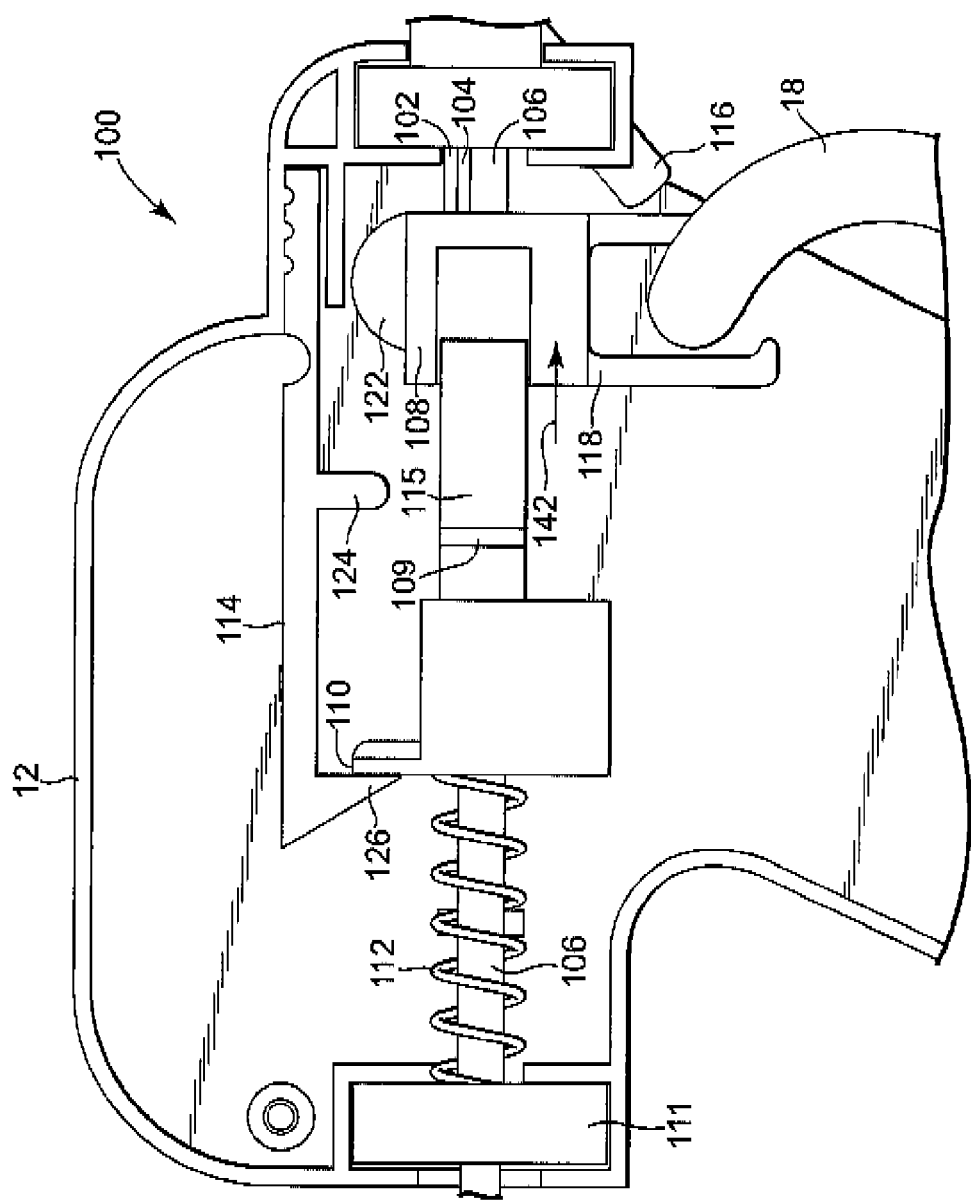

In FIG. 6G, needle block 108 continues to move forward while sheath block 110 stays in the same 6 mm position. At this point, the needles are fully deployed to the desired needle depth and the device is prepared to perform an ablation.

Figure 6H:
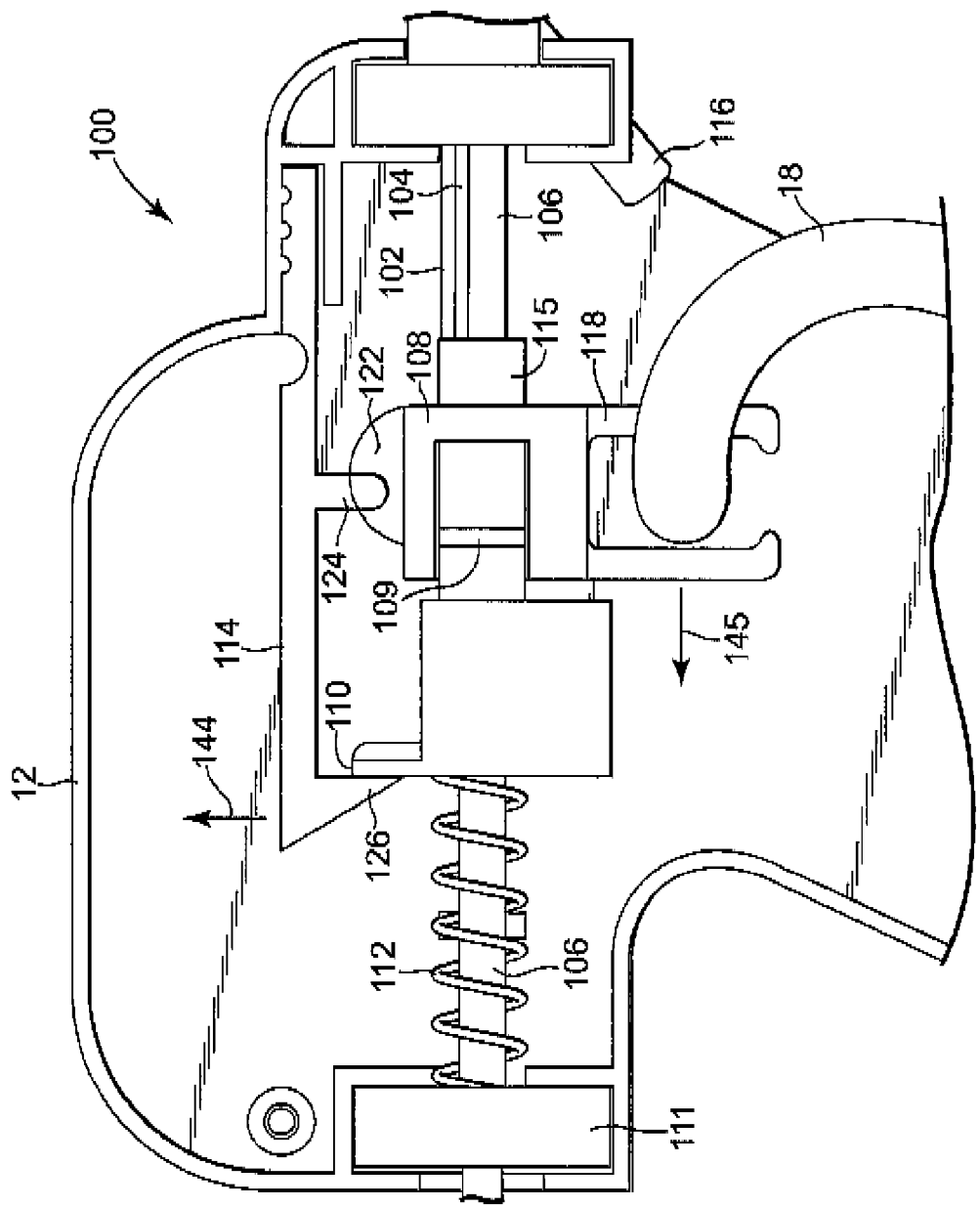
Figure 6J:
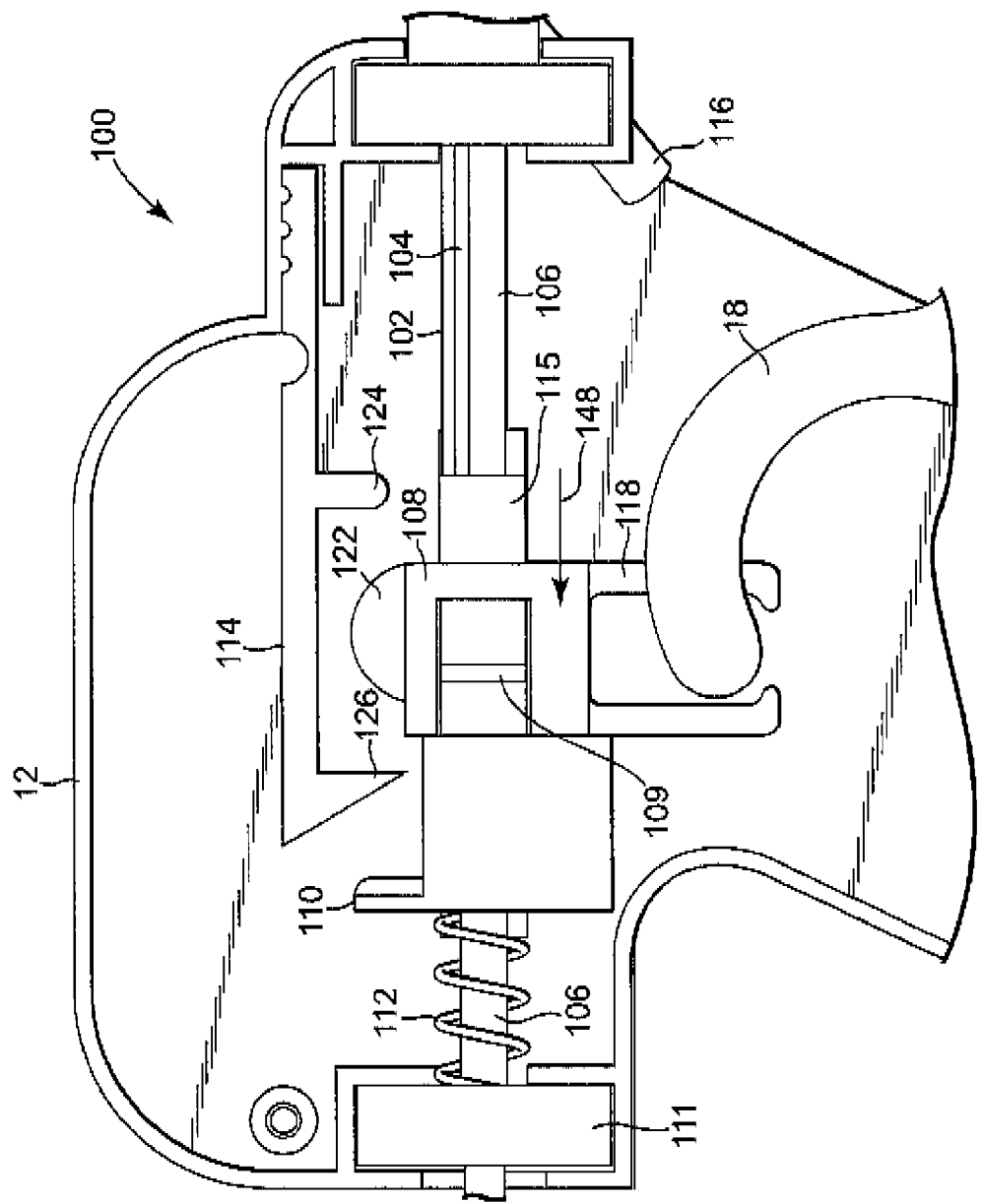

FIG. 6H is another side view of the needle deployment mechanism showing retraction of the needles. When an ablation is complete, the needles are retracted back into the catheter in preparation to reposition the device within or withdraw the device from the urethra. To retract the needles, the physician may move the lever 18 in the direction indicated by arrow 145. Alternatively, the physician may activate automatic retraction button 34 (see FIG. 1) to automatically retract the needles. As needle block 108 begins to move back, slide cap 122 hits protrusion 124 on 6 mm catch 114, which moves the 6 mm catch 114 upward in the direction indicated by arrow 144.

FIG. 6I shows that the sheath block 110 is now free of stop 126 and is pulled back by spring 112 to fully retract the sheaths. At the same time, needle block 108 continues to move backward as indicated by arrow 148 in FIG. 6J until it is butted up against sheath block 110. At this point both the needles and the sheaths are fully retracted.

Figure 7:
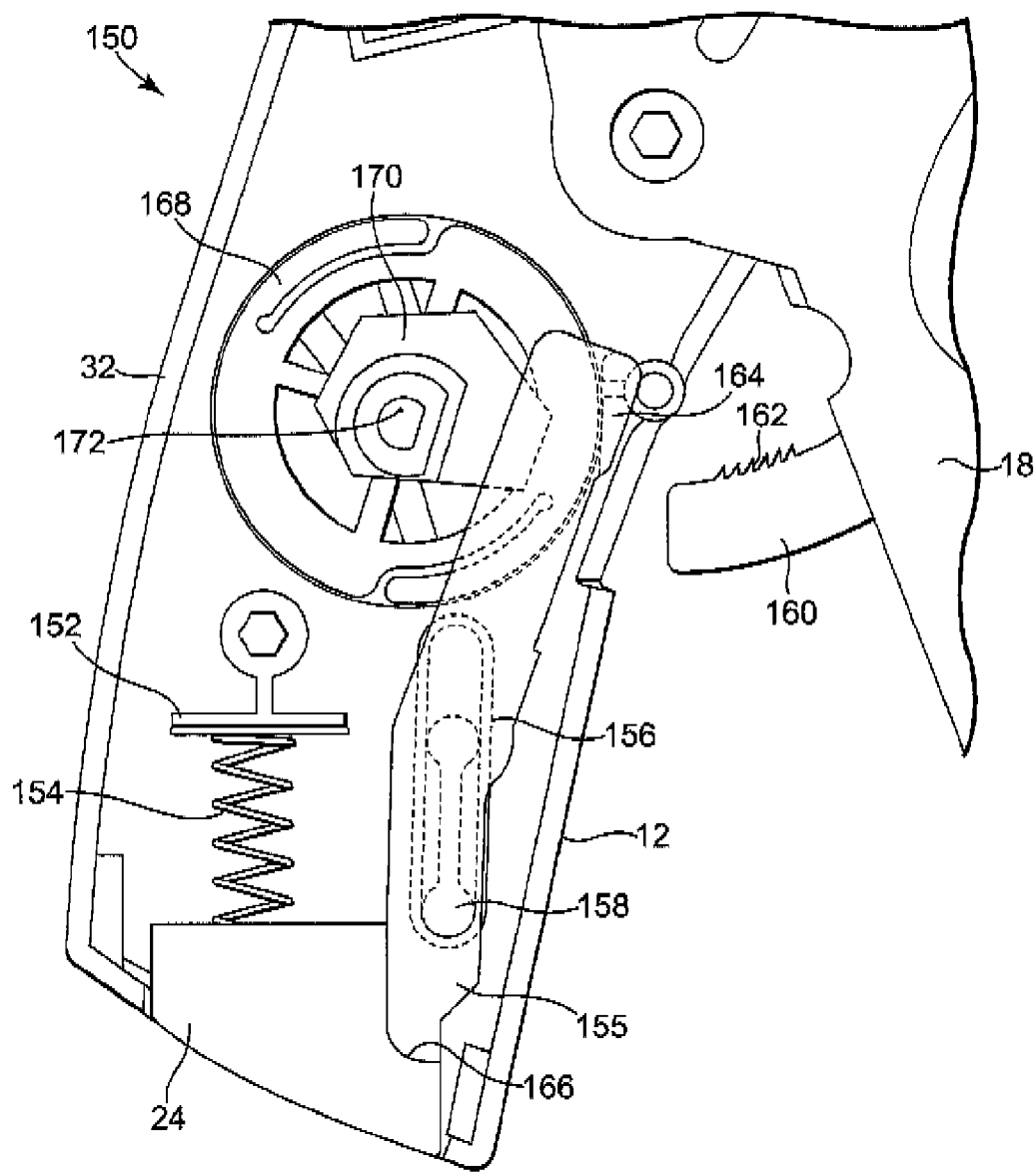
FIG. 7 is a diagram showing an automatic retraction mechanism for the device of FIG. 1.

FIG. 7 shows a side view of automatic needle retraction mechanism 150. In this embodiment, the automatic needle retraction mechanism is located inside the handle 32 of a TUNA device 10. Automatic needle retraction mechanism 150 includes a retraction button 24, retraction spring 154, and lever arm 155.

A lever engagement tooth 164 is located at the top of lever arm 155. As the physician actuates lever 18 to deploy the needles, ratchets 162 on lever extension 160 hit up against tooth 164. As the lever 18 continues to move, the interaction between tooth 164 and ratchets 162 produce a ratcheting effect. At the start of an ablation procedure, the physician determines the appropriate needle depth and manually rotates needle depth selector 22 (see FIG. 1) to the corresponding position. In FIG. 7, circular element 168 and needle depth key 170 are attached to and rotate along with the needle depth selector 22. Needle depth key 170 includes six faces, each face having a unique length as measured across the edge of the face. Each face also has a unique radius as measured from the edge of the face to center point 172 of the needle depth selector 22. As needle depth selector 22 is rotated, the face coming into contact with lever extension 160 changes based on the position of the dial. This causes lever engagement tooth 164 to engage the ratchet 162 corresponding to the needle depth as selected on the needle depth selector 22.

Once the needles have been deployed to the selected depth, tooth 164 holds lever 18 in place at the appropriate ratchet position 162 to maintain the selected needle depth. The needles and sheath are thus held in position by the interaction between tooth 164 and ratchets 162 while ablation energy is applied to the target prostate tissue.

When the needles are to be retracted, the physician may depress retraction button 24 to cause automatic retraction of the needles. Retraction button 24 is spring loaded with retraction spring 154. When retraction button 24 is depressed, spring 154 is compressed and ledge 166 presses up onto the base of lever arm 155. Ledge 166 pushes upwardly on lever arm 155 resulting in an upward movement of lever arm 155. During this upward movement, knobs 158 of lever arm 155 slide inside of track 156 located on the inside of housing 12. Upward movement of lever arm 155 results in upward movement of tooth 164, releasing ratchets 162. With no opposing force remaining to counteract it, the backward pulling force applied by spring 112 on the needle block 108 and sheath block 110 is then free to fully pull back and retract the needles and the sheaths as described above with respect to FIGS. 6H-6J.

Referring again to FIG. 1, in one embodiment, device 10 is a single-use, disposable device. The device may be constructed using mostly plastic parts, reducing the weight of and simplifying manufacture and assembly of the device.

Although the invention has been described generally with respect to a one piece, disposable TUNA device, it shall be understood that many of the features described herein may also be used with other conventional TUNA devices. For example, the simplified needle deployment mechanism may also be used in a conventional, TUNA device, such as those device with a reusable handle and replaceable catheter cartridge. The flexible catheter tip 60 may also be used with other types of TUNA devices. The automatic retraction mechanism described herein may also be incorporated into other types of TUNA devices and is not limited to use with the one piece, disposable device described herein.

The invention can provide a number of advantages. Because the device is designed for one-time use, sterilization is not required. This may minimize preparation time between procedures as well as result in higher patient throughput. In addition, the one-piece design of the device means that no pre-procedure assembly is required, further reducing preparation time. Furthermore, time spent maintaining the device may be reduced or eliminated as the device is used only once and then discarded. In addition, because the device may include a simplified design constructed of mostly plastic parts, the resulting TUNA device may be more reliable, easier to manufacture, lighter in weight and easier for the physician to operate and maneuver. These features may result in a transurethral ablation device that enables the physician for perform faster, more accurate, and more efficient TUNA procedures.

As another advantage, the flexible catheter tip may provide increased patient comfort during insertion of the catheter into the urethra. As another advantage, the single use lockout helps to ensure that the device is used on only a single patient. In this way, the patient receives the benefit of a dedicated TUNA device, increasing procedural safety.

As yet another advantage, the simplified needle deployment mechanism may result in a TUNA device that is more reliable, easier to manufacture, lighter and easier for the physician to maneuver. As yet another advantage, the automatic needle retraction mechanism helps ensure full retraction of the needles. The automatic needle retraction feature thus may increase the safety of the procedure by reducing the likelihood of inadvertent failure to fully retract the needles before the catheter is repositioned within or withdrawn from the urethra, thus reducing the likelihood of damage to the prostate or the urethra, and the associated increases in patient pain and recovery time.

Thus, the invention can reduce the complexity of the ablation procedure, while increasing efficiency, convenience and safety. The invention can also result in a procedure in which the risk of damage to the urethra, patient pain and recovery times are minimized, thus further promoting patient safety and procedural efficacy.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the present invention. The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for transurethral ablation, as described herein. These and other embodiments are within the scope of the following claims.

The invention claimed is:

1. A method comprising:
   advancing a needle block to deploy at least one ablation needle to a selected needle depth in response to actuation of a lever;
   advancing a sheath block to deploy an insulative sheath surrounding the at least one ablation needle to a first predetermined sheath depth in response to actuation of the lever;
   releasing a connection between the needle block and the sheath block; and
   retracting the sheath block after release of the connection, such that the sheath is retracted to a second predetermined sheath depth.

2. The method of claim 1, further comprising moving a catch in an upward direction during the advancing of the needle block to allow for the advancing of the sheath block.

3. The method of claim 2, further comprising moving the catch in a downward direction after the sheath block has advanced past the catch.

4. The method of claim 3, wherein retracting the sheath block further comprises retracting the sheath block until the sheath block is stopped by the catch such that the insulative sheath is retracted to the second predetermined sheath depth.

5. The method of claim 1, further comprising delivering ablation energy via the at least one ablation needle.

6. The method of claim 1, wherein advancing the needle block further comprises actuating a needle push rod that deploys the at least one ablation needle.

7. The method of claim 1, wherein advancing the sheath block further comprises actuating a sheath push rod that deploys the insulative sheath.

8. The method of claim 1, wherein releasing a connection further comprises releasing a snap fit that connects the needle block and the sheath block.

9. The method of claim 1, wherein advancing a needle block further comprises advancing the needle block until a selected face of a needle depth selector corresponding to the selected needle depth comes into contact with an extension of the lever.

10. The method of claim 9, wherein advancing the needle block further comprises engaging a lever engagement tooth with a ratchet corresponding to the selected needle depth.

11. The method of claim 1, further comprising applying a backward pulling force on the sheath block and the needle block to fully retract the at least one ablation needle and the insulative sheath within a transurethral catheter.

12. The method of claim 11, wherein applying a backward pulling force further comprises releasing a catch that maintains the sheath block at the second predetermined sheath depth.

13. A method comprising:
  advancing a needle block to deploy at least one ablation needle to a selected needle depth;
  advancing a sheath block to deploy an insulative sheath surrounding the at least one ablation needle to a first predetermined sheath depth;
  releasing a connection between the needle block and the sheath block;
  retracting the sheath block after release of the connection, such that the sheath is retracted to a second predetermined sheath depth that is less than the first predetermined needle depth; and
  delivering ablation energy to a prostrate of a patient via the at least one ablation needle.

14. The method of claim 13, wherein advancing the needle block further comprises advancing the needle block to deploy at least one ablation needle to the selected needle depth in response to actuation of a lever.

15. The method of claim 13, wherein advancing the sheath block further comprises advancing the sheath block to deploy the insulative sheath surrounding the at least one ablation needle to the first predetermined sheath depth in response to actuation of a lever.

16. The method of claim 13, wherein releasing a connection further comprises releasing a snap fit that connects the needle block and the sheath block.

17. The method of claim 16, wherein releasing the snap fit further comprises pushing back a set of tabs positioned on the sheath block to release the snap-fit between the needle block and the sheath block.

18. The method of claim 16, wherein retracting the sheath block after release of the connection further comprises applying a backward pulling force on the sheath block to retract the sheath to the second predetermined sheath depth.

19. The method of claim 13, further including rotating a needle depth key having a plurality of uniquely radiused faces each corresponding to a different one of a plurality of available needle depths.

20. The method of claim 19, further including actuating a lever such that a lever extension contacts one of the plurality of faces that corresponds to the selected needle depth.

* * * * *